United States Patent [19]

Coughlin et al.

[11] Patent Number: 5,976,860
[45] Date of Patent: Nov. 2, 1999

[54] CELL LINES INFECTED WITH GRANULOCYTIC EHRLICHIA, VACCINES, DIAGNOSTICS AND METHODS

[75] Inventors: Richard T. Coughlin, Leicester; Cindy Gingrich-Baker, Boylston, both of Mass.

[73] Assignee: Aquila Biopharmaceuticals, Inc., Framingham, Mass.

[21] Appl. No.: 08/613,415

[22] Filed: Mar. 11, 1996

Related U.S. Application Data

[63] Continuation-in-part of application No. 08/470,358, Jun. 6, 1995.

[51] Int. Cl.$^6$ .............................. C12N 5/00; C12N 1/00; C12N 1/12; C12N 1/04
[52] U.S. Cl. .................................. 435/240.2; 435/240.1; 435/243; 435/252.1; 435/260
[58] Field of Search .............................. 435/240.1, 240.2, 435/243, 252.1, 260

[56] References Cited

U.S. PATENT DOCUMENTS 5,192,679   3/1993   Dawson et al. ......................... 435/243

OTHER PUBLICATIONS

Winjum et al "In vitro proliferation of a canine granulocytic Ehrlichia" Veterinary Microbiology, 34 (1993) 355–362.
Anderson, B. E. et al., "*Ehrlichia chaffeensis*, a New Species Associated with Human Ehrlichiosis," *J. Clin. Microbiol.* 29(12):2838–2842 (1991).
Bakken, J. S. et al., "Human Granulocytic Ehrlichiosis in the Upper Midwest United States: A New Species Emerging?," *J. Amer. Med. Assoc.* 272(3):212–218 (Jul. 1994).
Brouqui, P. et al., "Cytopathic Effect, Plaque Formation, and Lysis of *Ehrlichia chafeensis* Grown on Continuous Cell Lines," *Inf. Immun.* 62(2):405–411 (Feb. 1994).
Chen, S.–M. et al., "Identification of a Granulocytotropic Ehrlichia Species as the Etiologic Agent of Human Disease," *J. Clin. Microbiol.* 32(3):589–595 (Mar. 1994).
Collins, S. J. et al., "Continuous growth and differentiation of human myeloid leukaemic cells in suspension culture," *Nature* 270:347–348 (1977).
Eremeeva, M. et al., "Differentiation among Spotted Fever Group Rickettsiae Species by Analysis of Restriction Fragment Length Polymorphism of PCR–Amplified DNA," *J. Clin. Microbiol.* 32(3):803–810 (Mar. 1994).
Goodman, J. L. et al., "Direct Cultivation of the Causative Agent of Human Granulocytic Ehrlichiosis," *New Eng. J. Med.* 334(4):209–215 (Jan. 1996).
Holland, C. J. et al., "Isolation, Experimental Transmission, and Characterization of Causative Agent of Potomac Horse Fever," *Science* 227:522–524 (1985).
Jongejan, F., "Protective Immunity to Heartwater (*Cowdria ruminantium* Infection) Is Acquired after Vaccination with In Vitro–Attenuated Rickettsiae," *Inf. Immun.* 59(2):729–731 (1991).

Kakoma, I. et al., "Cultural, Molecular, and Immunological Characterization of the Etiologic Agent for Atypical Canine Ehrlichiosis," *J. Clin. Microbiol.* 32(1):170–175 (Jan. 1994).
Lewis, G. E., "Equine Ehrlichiosis: A Comparison between *E. equi* and Other Pathogenic Species of Ehrlichia," *Vet. Parasitol.* 2:61–74 (1976).
Mather, T. N. et al., "Competence of dogs as reservoirs for Lyme disease spirochetes (*Borrelia burgdorferi*)," *J. Amer. Vet. Med. Assoc.* 205(2):186–188 (Jul. 1994).
Mather, T. N. et al., "*Borrelia burgdorferi* and *Babesia microti*: Efficiency of Transmission from Reservoirs to Vector Ticks (*Ixodes dammini*)," *Exp. Parasitol.* 70:55–61 (1990).
McDade, J. E., "Ehrlichiosis—A Disease of Animals and Humans," *J. Inf. Dis.* 161:609–617 (1990).
Palmer, J. E., "Prevention of Potomac Horse Fever," *Cornell Vet.* 79(3):201–205 (1989).
Rikihisa, Y., "The Tribe Ehrlichieae and Ehrlichial Diseases," *Clin. Microbiol. Rev.* 4(3):286–308 (1991).
Ristic, M. and D. L. Huxsoll, in *Bergey's Manual of Sytematic Bacteriology*, Krieg, N. et al., eds., Williams and Wilkins:Baltimore pp. 704–709 (1986).
Rynkiewicz, D. L. et al., "Human Ehrlichiosis in New England," *New Eng. J. Med.* 330(4):292–293 (Jan. 1994).
Sells, D. M. et al., "Ultrastructural Observations on *Ehrlichia equi* Organisms in Equine Granulocytes," *Inf. Immun.* 13(1):273–280 (1976).
Stockham, S. L. et al., "Evaluation of granulocytic ehrlichiosis in dogs of Missouri, including serologic status to *Ehrlichia canis, Ehrlichia equi,* and *Borrelia burgdorferi,*" *Amer. J. Vet. Res.* 53(1):63–68 (1992).
Weisburg, W. G. et al., "Phylogenetic Diversity of Rickettsiae," *J. Bacteriol.* 171(8):4202–4206 (1989).
Weiss, E. et al., "Substrate Utilization by *Ehrlichia sennetsu* and *Ehrlichia risticii* Separated from Host Constituents by Renografin Gradient Centrifugation," *J. Bacteriol.* 170(11):5012–5017 (1988).

*Primary Examiner*—James C. Housel
*Assistant Examiner*—Rodney P. Swartz
*Attorney, Agent, or Firm*—Hale and Dorr LLP

[57] ABSTRACT

The present invention relates, in general, to granulocytic Ehrlichia. In particular, the present invention relates to a cell line selected from the group consisting of a promyelocytic leukemia cell line, an acute myelogenous leukemia cell line, a histiocytic lymphoma cell line, a monocyte macrophage-like cell line, an acute monocytic leukemia cell line, and an embryonic lung cell line wherein the cell line is infected with granulocytic Ehrlichia, a method of continually growing granulocytic Ehrlichia, vaccines comprising granulocytic Ehrlichia or granulocytic Ehrlichia antigens, methods of preventing ehrlichiosis in an animal, antibodies to granulocytic Ehrlichia, and methods for identifying granulocytic Ehrlichia in an animal.

34 Claims, 3 Drawing Sheets

CELL LINES INFECTED WITH GRANULOCYTIC EHRLICHIA, VACCINES, DIAGNOSTICS AND METHODS

CROSS-REFERENCE TO RELATED APPLICATION

This application is a continuation-in-part of U.S. patent application Ser. No. 08/470,358, filed Jun. 6, 1995, the contents of which are incorporated herein by reference.

BACKGROUND OF THE INVENTION

1. Field of the Invention

The present invention relates, in general, to granulocytic Ehrlichia. In particular, the present invention relates to a cell line selected from the group consisting of a promyelocytic leukemia cell line, an acute myelogenous leukemia cell line, a histiocytic lymphoma cell line, a monocyte macrophage-like cell line, an acute monocytic leukemia cell line, and an embryonic lung cell line wherein the cell line is infected with granulocytic Ehrlichia, a method of continually growing granulocytic Ehrlichia, vaccines comprising granulocytic Ehrlichia or granulocytic Ehrlichia antigens, methods of preventing ehrlichiosis in an animal, antibodies to granulocytic Ehrlichia, and methods for detecting granulocytic Ehrlichia or antibodies to granulocytic Ehrlichia in an animal.

2. Related Art

A wide range of virus, bacteria and parasites are transmitted to mammals by ticks. In the United States, Lyme disease is the most frequently reported tick borne disease. The etiologic agent of Lyme disease, *B. burgdorferi,* is transmitted by ticks of the genus Ixodes (Mather et al., *JAVMA* 205:186–188 (1994)).

Another tick borne disease, ehrlichiosis, is caused by the genera of bacteria known as Ehrlichia (for review of Ehrlichia and Ehrlichia diseases see, Rikihisa, *Clin. Microbiol. Reviews* 4(3):286–308 (1991)). The various species of Ehrlichia are all members of the family of Rickettsiaceae. Unlike *B. burgdorferi,* Ehrlichia do not require a mammalian host to maintain themselves in the wild. However, if a mammalian host is involved, most Ehrlichia species infect monocytes of the blood and in several cases have been isolated in monocyte cell culture (see, for example, Dawson et al., U.S. Pat. No. 5,192,679 issued Mar. 9, 1993 which claims a canine monocyte macrophage cell line DH82 infected with *E. canis*).

*Ehrlichia equi* is the causative agent of equine ehrlichiosis (Rikihisa, *Clin. Microbiol. Reviews* 4(3):286–308 (1991)). Although the transmission mechanism has not been defined, it appears to be unusual in that it infects granulocytes and not monocytes. *E. equi* has a broad range of hosts. Experimental infection of horses, burros, sheep goats, dogs, cats, monkeys, and baboons has been reported (Lewis, *Vet. Parasitol.* 2:61–74 (1976)). In Europe, another granulocytic Ehrlichia, *E. phagocytophila,* causes tick borne fever in sheep, cattle, and bison, and is vectored by *I. ricinis* (Ristic, M. et al., in *Bergey's Manual of Systemic Bacteriology,* Kreig, N. et al., eds., Williams and Wilkins, Baltimore (1984), pp. 704–709). Although these organisms are carried by different ticks and are reported on different continents, they are indistinguishable from one another by serologic or PCR methods (Chen et al., *J. Clin. Microbiol.* 32:589–595 (1994)). Recently, several fatal cases of human granulocytic Ehrlichosis have been reported in Wisconsin, Minnesota, and Connecticut as well as a non-fatal human case in Florida (Chen et al., *J. Clin. Microbiol.* 32:589–595 (1994)). These cases of ehrlichiosis were caused by an Ehrlichia that was indistinguishable from *E. equi* and *E. phagocytophila* by PCR methods (Bakken, J. S. et al., *JAMA* 272:212–218 (1994); Rynkiewicz and Liu, *New Engl. J. Med.* 330:292–293 (1994)).

SUMMARY OF THE INVENTION

Unlike *E. canis,* there are no reports of cell culture conditions for the isolation of *E. equi, E. phagocytophila,* or human granulocytic Ehrlichia, nor is there an animal model for transmission. Both the cell culture and transmission model are essential in the development of appropriate antibiotic therapy and in vaccine development, as well as in the development of reliable diagnostic products.

The invention further provides a method of continually growing granulocytic Ehrlichia comprising infecting a cell line selected from the group consisting of a promyelocytic leukemia cell line, an acute myelogenous leukemia cell line, a histiocytic lymphoma cell line, a monocyte macrophage-like cell line, an acute monocytic leukemia cell line, and an embryonic lung cell line with granulocytic Ehrlichia and cultivating the infected cell line in a suitable culture medium.

Thus, the present invention provides a cell line selected from the group consisting of a promyelocytic leukemia cell line, an acute myelogenous leukemia cell line, an histiocytic lymphoma cell line, a monocyte macrophage-like cell line, an acute monocytic leukemia cell line, and an embryonic lung cell line wherein the cell line is infected with granulocytic Ehrlichia.

The invention also provides vaccine comprising granulocytic Ehrlichia together with a pharmaceutically acceptable diluent, carrier, or excipient, wherein the granulocytic Ehrlichia is present in an amount effective to elicit protective immune responses in an animal to granulocytic Ehrlichia.

The invention further provides a vaccine comprising an granulocytic Ehrlichia antigen(s) together with a pharmaceutically acceptable diluent, carrier, or excipient, wherein the antigen is present in an amount effective to elicit protective antibodies in an animal to granulocytic Ehrlichia.

The invention also provides a method of preventing ehrlichiosis in an animal comprising administering to the animal the above-described vaccine.

The invention further provides a method for identifying granulocytic Ehrlichia in an animal comprising analyzing tissue or body fluid from the animal for a nucleic acid, protein, polysaccharide, or antibody specific to granulocytic Ehrlichia.

The invention also provides a substantially pure granulocytic Ehrlichia antigen having an approximate molecular weight selected from the group consisting of 21 kDa, 23 kDa, 40 kDa, 47 kDa, 85 kDa, 130 kDa, and 145 kDa.

The invention further provides a substantially pure polypeptide comprising the above-described antigen.

The invention also provides an isolated nucleic acid molecule coding for a polypeptide comprising the above-described antigen.

The invention further provides an antibody having binding affinity to the above-described antigen.

The invention also provides an antibody having binding affinity to the above-described antigen and/or polypeptide.

The invention further provides a nucleic acid probe for the detection of the presence of granulocytic Ehrlichia nucleic acid in a sample from an individual comprising a nucleic acid molecule sufficient to specifically detect under stringent hybridization conditions the presence of the above-described molecule in the sample.

The invention also provides a method of detecting granulocytic Ehrlichia nucleic acid in a sample comprising:

a) contacting the sample with the above-described nucleic acid probe, under conditions such that hybridization occurs, and b) detecting the presence of the probe bound to granulocytic Ehrlichia nucleic acid.

The invention further provides a kit for detecting the presence of granulocytic Ehrlichia nucleic acid in a sample comprising at least one container means having disposed therein the above-described nucleic acid probe.

The invention also provides a diagnostic kit for detecting the presence of granulocytic Ehrlichia in a sample comprising at least one container means having disposed therein the above-described antibody.

The invention also provides a diagnostic kit for detecting the presence of antibodies to Ehrlichia in a sample comprising at least one container means having disposed therein the above-described antigen(s).

Further objects and advantages of the present invention will be clear from the description that follows.

DETAILED DESCRIPTION OF THE PREFERRED EMBODIMENTS

Figure 1:
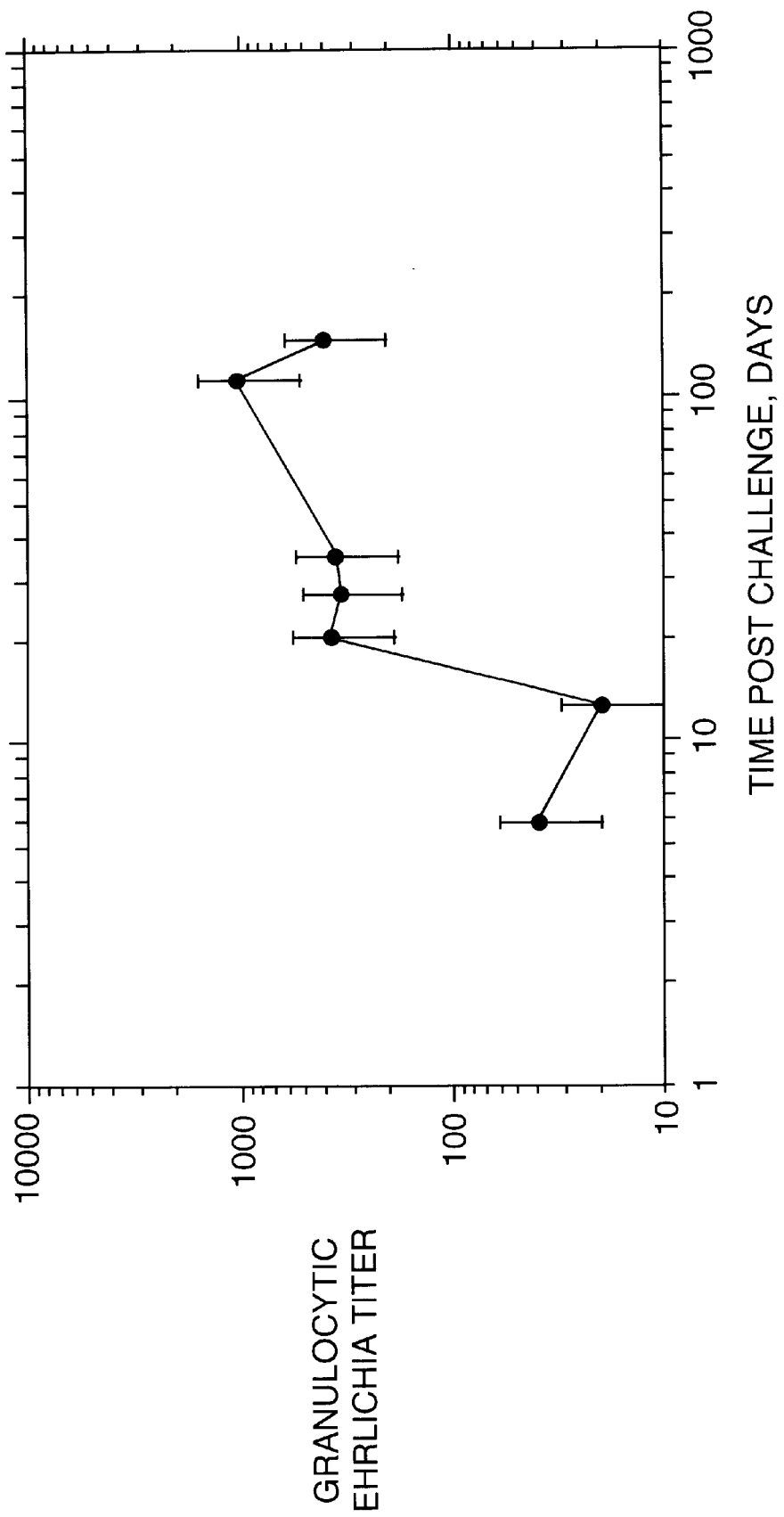
FIG. 1. Granulocytic Ehrlichia specific antibody titers of infected dogs.

The present invention relates to granulocytic Ehrlichia.

In one preferred embodiment, the present invention relates to granulocytic Ehrlichia isolated from a host wherein said host is a mammal (preferably, a human, dog, mouse, or horse). In a preferred embodiment, the granulocytic Ehrlichia is isolated from a human host.

In one embodiment, the present invention relates to a promyelocytic leukemia cell line infected with granulocytic Ehrlichia. In a preferred embodiment, the promyelocytic leukemia cell line is a human cell line. In a preferred embodiment, the human promyelocytic leukemia cell line is HL-60 (ATCC CCL 240) or mutants or variants thereof. In another preferred embodiment, the human promyelocytic leukemia cell line infected with granulocytic Ehrlichia has the identifying characteristics of ATCC CRL-11864 (Cell line XQH), ATCC CRL-11865 (Cell line VXG3), or mutants or variants thereof. ATCC CRL-11864 (Cell line XQH) and ATCC CRL-11865 (Cell line VXG3) were deposited at the American Type Culture Collection (ATCC), 12301 Parklawn Drive, Rockville, Md. 20852 USA on Mar. 29, 1995.

The identifying characteristics of ATCC CRL-11864, ATCC CRL-11865, or mutants or variants thereof are defined herein to include characteristics which are commonly shared among granulocytic Ehrlichia strains, including physiological, morphological, and chemically-based characteristics. In addition to the two deposited cell lines infected, Table 3 shows seven more HL60 cell lines that were infected by whole blood or isolated white blood cells from individual dogs that were infected with granulocytic Ehrlichia.

In another embodiment, the present invention relates to an acute myelogenous leukemia cell line (preferably, a human cell line) infected with granulocytic Ehrlichia. In a preferred embodiment, the human acute myelogenous leukemia cell line is KG-1 (ATCC CCL-246) or mutants or variants thereof.

In another embodiment, the present invention relates to histiocytic lymphoma cell line (preferably, a human cell line) infected with granulocytic Ehrlichia. In a preferred embodiment, the human histiocytic lymphoma cell line is U937 (ATCC CRL-1593.2) or mutants or variants thereof.

In another embodiment, the present invention relates to a monocyte macrophage-like cell line (preferably, a human cell line) infected with granulocytic Ehrlichia. In a preferred embodiment, the human monocyte macrophage-like cell line is THP-1 (ATCC TIB-202) or mutants or variants thereof.

In another embodiment, the present invention relates to an acute monocytic leukemia cell line (preferably, a human cell line) infected with granulocytic Ehrlichia. In a preferred embodiment, the human acute monocytic leukemia cell line is AML-193 (ATCC CRL-9589) or mutants or variants thereof.

In another embodiment, the present invention relates to an embryonic lung cell line (preferably, a human cell line) infected with granulocytic Ehrlichia. In a preferred embodiment, the human embryonic lung cell line is HEL299 (ATCC CCL-137) or mutants or variants thereof.

Mutants and variants of the cell lines containing granulocytic Ehrlichia or of the granulocytic Ehrlichia organism contained therein, include any detectable change in the genetic material which can be transmitted to daughter cells and possibly even to succeeding generations giving rise to mutant cells or mutant individuals. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens.

Mutations may be induced by chemical agents such as alkylating agents, nitrous acid, acridine dyes, by recombinant DNA methods using nucleic acid base analogs, etc., or through environmental changes such as radiation, metabolic substrate changes, etc. (*Principles of Genetics,* 8th Edition, Gardner, E. J. et al., eds., John Wiley & Sons, New York 1991, pp. 288–319). Since this is an intracellular organism, the granulocytic Ehrlichia can be altered by reisolation on another host cell line with a different phenotype. Mutations may also occur spontaneously. In two of the cell lines, the normal cytopathic effect of granulocytic Ehrlichia was observed to be lost through serial passage. Such phenotypic mutants are valuable in that they are easier to maintain in cell culture.

In another embodiment, the present invention relates to a method of continually growing granulocytic Ehrlichia comprising infecting a cell line selected from the group consisting of a promyelocytic leukemia cell line, an acute myelogenous leukemia cell line, a histiocytic lymphoma cell line, a monocyte macrophage-like cell line, an acute monocytic leukemia cell line, and an embryonic lung cell line with granulocytic Ehrlichia and cultivating the infected cell line in a suitable culture medium. See for example, Collins et al., *Nature* 270:347–349 (1977)).

In a further embodiment, the present invention relates to a vaccine comprising granulocytic Ehrlichia together with a pharmaceutically acceptable diluent, carrier, or excipient, wherein the granulocytic Ehrlichia is present in an amount effective to elicit a protective immune response in an animal to granulocytic Ehrlichia. Granulocytic Ehrlichia may be purified from the infected cell lines described above using techniques well known in the art. Isolation of mammalian cell-free Ehrlichia was accomplished as described in Example 2. Methods of obtaining mammalian cell-free *Ehrlichia chaffeensis* are also appropriate for the isolation of mammalian cell-free granulocytic Ehrlichia (Brouqui, P. et al., *Infect. Immun.* 62:405–11 (1994)).

The granulocytic Ehrlichia present in the vaccine may be not viable (e.g. may be heat killed) or may be attenuated. Heat killed granulocytic Ehrlichia vaccines may be prepared as previously described for other heat killed vaccines (See, for example, Palmer, *Cornell Vet.* 79:201–205 (1989) which describes a vaccine prepared from an inactivated cell culture of *Ehrlichia risticii*). Likewise, attenuated granulocytic Ehrlichia vaccines may be prepared as previously described for other attenuated live vaccines (See, for example, Jongejan, *Infect. Immun.* 59:729–731 (1991) which describes protective immunity to *C. ruminantium* after vaccination with in-vitro attenuated rickettsiae).

In another embodiment, the present invention relates to a vaccine comprising a granulocytic Ehrlichia antigen(s) together with a pharmaceutically acceptable diluent, carrier, or excipient, wherein the antigen is present in an amount effective to elicit a protective immune response in an animal to granulocytic Ehrlichia. Antigens of granulocytic Ehrlichia may be obtained using methods well known in the art.

Crude antigens can be prepared from infected host cells by chemical fixation, heat inactivation, irradiation, sonication, freeze thaw, or other means. Less crude antigens could be obtained from bacteria released into the culture media from lysed cells and then similarly inactivated. Partially purified and purified granulocytic Ehrlichia antigens can be obtained by well-known methods including centrifugation, phase partition, and column chromatography. (Brouqui, P. et al., *Infect. Immun.* 62:405–11 (1994).)

In a preferred embodiment, the antigens are proteins, polysaccharides or lipids. In a further preferred embodiment, the protein, polysaccharide or lipid are present on the surface of granulocytic Ehrlichia. In another preferred embodiment, the granulocytic Ehrlichia protein-antigen is conjugated to an Ehrlichia capsular polysaccharide (CP) to produce a double vaccine. CPs, in general, may be prepared or synthesized as described in Schneerson et al. *J. Exp. Med.* 152:361–376 (1980); Marburg et al. *J. Am. Chem. Soc.* 108:5282 (1986); Jennings et al., *J. Immunol.* 127:1011–1018 (1981); and Beuvery et al., *Infect. Immunol.* 40:39–45 (1983). In a further preferred embodiment, the present invention relates to a method of preparing a polysaccharide conjugate comprising: obtaining the above-described Ehrlichia antigen; obtaining a CP or fragment from Ehrlichia; and conjugating the antigen to the CP or CP fragment.

In a preferred embodiment, the present invention relates to a substantially pure granulocytic Ehrlichia antigen having an approximate molecular weight selected from the group consisting of 21 kDa, 23 kDa, 40 kDa, 47 kDa, 85 kDa, 130 kDa, and 145 kDa. These antigens can be purified from Ehrlichia cultures or produced with recombinant nucleic acid methods. The present invention is intended to cover fragments and synthetic peptides of these antigens.

In another preferred embodiment, the present invention relates to a substantially pure polypeptide comprising the above-described antigen.

In another preferred embodiment, the present invention relates to an isolated nucleic acid molecule coding for a polypeptide comprising the above-described antigen(s).

In another preferred embodiment, the present invention relates to an antibody having binding affinity to the above-described antigen(s).

In another preferred embodiment, the present invention relates to an antibody having binding affinity to the above-described polypeptide.

In another preferred embodiment, the present invention relates to a nucleic acid probe for the detection of the presence of granulocytic Ehrlichia nucleic acid in a sample from an individual comprising a nucleic acid molecule sufficient to specifically detect under stringent hybridization conditions the presence of the above-described molecule in the sample.

In another preferred embodiment, the present invention relates to a method of detecting granulocytic Ehrlichia nucleic acid in a sample comprising:

a) contacting the sample with the above-described nucleic acid probe, under conditions such that hybridization occurs, and b) detecting the presence of the probe bound to granulocytic Ehrlichia nucleic acid.

In another preferred embodiment, the present invention relates to a diagnostic kit for detecting the presence of granulocytic Ehrlichia nucleic acid in a sample comprising at least one container means having disposed therein the above-described nucleic acid probe.

In another preferred embodiment, the present invention relates to a diagnostic kit for detecting the presence of granulocytic Ehrlichia antigens in a sample comprising at least one container means having disposed therein the above-described antibodies.

In another preferred embodiment, the present invention relates to a diagnostic kit for detecting the presence of antibodies to granulocytic Ehrlichia antigens in a sample comprising at least one container means having disposed therein the above-described antigens.

In a preferred embodiment, the animal to be protected is selected from the group consisting of humans, horses, deer, cattle, pigs, sheep, dogs, and chickens. In a more preferred embodiment, the animal is a human or a dog.

In a further embodiment, the present invention relates to a method of preventing ehrlichiosis in an animal comprising administering to the animal the above-described vaccine, wherein the vaccine is administered in an amount effective to prevent Ehrlichiosis. The vaccine of the invention is used in an amount effective depending on the route of administration. Although intranasal, subcutaneous or intramuscular routes of administration are preferred, the vaccine of the present invention can also be administered by an oral, intraperitoneal or intravenous route. One skilled in the art will appreciate that the amounts to be administered for any particular treatment protocol can be readily determined without undue experimentation. Suitable amounts are within the range of 2 micrograms of the protein per kg body weight to 100 micrograms per kg body weight.

Further, live attenuated strains of granulocytic Ehrlichia can be used as vaccines, as is done with *Brucella abortus* (Brucellosis vaccine, Coopers, U.S. Vet. Lic. No: 107). The non-cytopathic cell lines, VOG and XUG, can be suitable as attenuated vaccines.

The vaccine can be delivered through a vector such as BCG. The vaccine can also be delivered as naked DNA coding for target antigens.

The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the vaccine has suitable solubility properties. The vaccines may be in the form of single dose preparations or in multi-dose flasks which can be used for mass vaccination programs. Reference is made to Remington's *Pharmaceutical Sciences,* Mack Publishing Co., Easton, Pa., Osol (ed.) (1980); and *New Trends and Developments in Vaccines,* Voller et al. (eds.), University Park Press, Baltimore, Md. (1978), for methods of preparing and using vaccines.

The vaccines of the present invention may further comprise adjuvants which enhance production of antibodies and immune cells. Such adjuvants include, but are not limited to, various oil formulations such as Freund's complete adjuvant (CFA), the dipeptide known as MDP, saponins (ex. QA-21, U.S. Pat. No. 5,047,540), aluminum hydroxide, or lymphatic cytokines. Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Vaccine may be absorbed onto the aluminum hydroxide from which it is slowly released after injection. The vaccine may also be encapsulated within liposomes according to Fullerton, U.S. Pat. No. 4,235,877.

In a further embodiment, the present invention relates to a method for identifying granulocytic Ehrlichia in an animal comprising analyzing tissue or body fluid from the animal for a nucleic acid, protein, polysaccharide, lipid, or antibody specific to granulocytic Ehrlichia. Analysis of nucleic acid specific to granulocytic Ehrlichia can be by PCR techniques or hybridization techniques (cf. *Molecular Cloning: A Laboratory Manual, second edition,* edited by Sambrook, Fritsch, & Maniatis, Cold Spring Harbor Laboratory, 1989; Eremeeva et al., *J. Clin. Microbiol.* 32:803–810 (1994) which describes differentiation among spotted fever group Rickettsiae species by analysis of restriction fragment length polymorphism of PCR-amplified DNA). Nucleic acid probes used to analyze granulocytic Ehrlichia genomic DNA via PCR analysis have been described in Chen et al., *J. Clin. Microbiol.* 32:589–595 (1994).

Proteins, polysaccharides, or antibodies specific to granulocytic Ehrlichia may be identified as described in *Molecular Cloning: A Laboratory Manual, second edition,* Sambrook et al., eds., Cold Spring Harbor Laboratory (1989). More specifically, antibodies may be raised to proteins specific to granulocytic Ehrlichia as generally described in *Antibodies: A Laboratory Manual,* Harlow and Lane, eds., Cold Spring Harbor Laboratory (1988). Granulocytic Ehrlichia-specific antibodies can also be obtained from infected animals (Mather, T. et al., *JAMA* 205:186–188 (1994)).

In another embodiment, the present invention relates to an antibody having binding affinity specifically to a granulocytic Ehrlichia antigen as described above. The granulocytic Ehrlichia antigen of the present invention can be used to produce antibodies or hybridomas. One skilled in the art will recognize that if an antibody is desired, a peptide can be generated as described herein and used as an immunogen. The antibodies of the present invention include monoclonal and polyclonal antibodies, as well as fragments of these antibodies. The invention further includes single chain antibodies. Antibody fragments which contain the idiotype of the molecule can be generated by known techniques, for example, such fragments include but are not limited to: the F(ab')$_2$ fragment; the Fab' fragments, Fab fragments, and Fv fragments.

Of special interest to the present invention are antibodies to granulocytic Ehrlichia antigens which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988). General reviews of "humanized" chimeric antibodies are provided by Morrison, S. L. (*Science,* 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of antigen used for immunization will vary based on the animal which is immunized, the antigenicity of the antigen and the site of injection.

The antigen may be modified or administered in an adjuvant in order to increase the peptide antigenicity. Methods of increasing the antigenicity of an antigen are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and cultured to produce monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)). Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, NY, pp. 289–307 (1992), *Antibodies: A Laboratory Manual*, Harlow and Lane, eds., Cold Spring Harbor Laboratory (1988) and Kaspczak et al., *Biochemistry* 28:9230–8 (1989).

In another embodiment, the present invention relates to a method of detecting a granulocytic Ehrlichia antigen in a sample, comprising: a) contacting the sample with an above-described antibody, under conditions such that immunocomplexes form, and b) detecting the presence of said antibody bound to the antigen. In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985); and *Antibodies: A Laboratory Manual*, Harlow and Lane, eds., Cold Spring Harbor Laboratory (1988).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is capable with the system utilized.

In another embodiment, the present invention relates to a method of detecting the presence of antibodies to granulocytic Ehrlichia in a sample, comprising: a) contacting the sample with an above-described antigen, under conditions such that immunocomplexes form, and b) detecting the presence of said antigen bound to the antibody. In detail, the methods comprise incubating a test sample with one or more of the antigens of the present invention and assaying whether the antigen binds to the test sample. Methods of antibody detection are meant to include whole cell or fixed cell immunoflorescence (IFA), Western blot analysis, EIA, and RIA.

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits.

One skilled in the art will readily recognize that the antibodies described in the present invention can readily be incorporated into one of the established kit formats which are well known in the art.

The diagnostic and screening methods of the invention are especially useful for a patient suspected of being at risk for developing or having ehrlichiosis. According to the invention, presymptomatic screening of an individual in need of such screening is now possible using DNA encoding an antigen of the invention. The screening method of the invention allows a presymptomatic diagnosis of the presence of the DNA in individuals, and thus an opinion concerning the likelihood that such individual would develop or has developed ehrlichiosis. Early diagnosis is desired to maximize appropriate timely intervention.

In one preferred embodiment of the method of screening, a tissue sample would be taken from such individual, and screened for (1) the presence of a granulocytic Ehrlichia specific gene; (2) the presence of granulocytic Ehrlichia specific mRNA and/or (3) the presence of a granulocytic Ehrlichia specific antigen (ex. protein). The granulocytic Ehrlichia specific gene can be characterized based upon, for example, detection of restriction digestion patterns in "normal" versus the patient's DNA, including RFLP analysis, using DNA probes prepared against the genes sequence (or a functional fragment thereof) taught in the invention. Similarly, granulocytic Ehrlichia specific mRNA can be characterized and compared to mRNA in a sample. The technique of PCR may be used to conduct the above-described analyses. Granulocytic Ehrlichia specific antigens/proteins can also be detected using a biological assay for the antigen's activity or using an immunological assay and antibodies. When assaying granulocytic Ehrlichia specific antigens/proteins, the immunological assay is preferred for its speed. See, *Antibodies: A Laboratory Manual,* Harlow and Lane, eds., Cold Spring Harbor Laboratory (1988).

The present invention is described in further detail in the following non-limiting examples.

EXAMPLE 1

Transmission of Granulocytic Ehrlichia

Adult *I. scapularis* ticks were collected from areas on the East Coast of the United States that have high incidence of human Lyme disease, Westchester County, NY and Montgomery County, PA. The prevalence of *B. burgdorferi* sensu stricto infection in the ticks was determined by direct fluorescence immunoassay (Mather, T. et al., *Exp. Parasitol.* 70:55–61 (1990)) of tick midguts to be 11/30 (35%) and 16/30 (55%), respectively. Four to five adult female and an equal number of male ticks from each collection site were applied to the dogs as previously described (Mather et al., *JAVMA* 205(2):186–188 (1994)). At the time the study was performed, it was not possible to determine the prevalence of Ehrlichia infection in the ticks.

Blood chemistries and hematology were performed before and after challenge. Borrelia infection of the dogs was confirmed by the progressive development of Western blot reactivity (Cambridge Biotech Corp.). Babesia, Rocky Mountain Spotted Fever (RMSF), and Ehrlichia infection were determined by IFA using sera from dogs before and after challenge. Table 1 shows that none of the dogs tested demonstrated serological evidence of infection with *B. microti, B. gibsonii,* or *Rickettsiella rickettsii* either before or after challenge. One dog (EIP) was weakly positive for antibodies to *E. canis* but was seronegative when examined after challenge. It was concluded that the dog had not been infected with *E. canis.* One dog (DXP) became weakly seropositive for antibodies to *Babesia canis* after challenge. Seven of the 11 dogs were seropositive for antibodies to *E. equi* after challenge. None of these dogs were seropositive for antibodies to *E. equi* prior to challenge. Sera was also tested for cross reaction with other Ehrlichia species. Sera reactive with *E. equi* (granulocytic Ehrlichia) were unreactive with *E. sennetsu, E. risticii,* or *E. platys.* With few exceptions, sera reactive with *E. equi* were also unreactive with *E. canis.* Cross reaction with *E. canis* was very weak ($\leq 1:80$) and was only seen with sera that had the highest *E. equi* reactivity ($\geq 1:1280$).

Following challenge hematologic parameters of the dogs that were infected with a granulocytic Ehrlichia that is serologically cross-reactive with *E. equi,* were compared to those dogs that were not infected. The results shown in Table 2 indicate that prior to challenge there were no significant differences in the blood cell counts between the dogs that eventually became infected with granulocytic Ehrlichia and those that did not become infected. After challenge, the granulocytic Ehrlichia infected dogs had reduced neutrophil and elevated lymphocyte counts consistent with ehrlichiosis.

FIG. 1 shows that the granulocytic Ehrlichia specific antibody titers of infected dogs remained elevated long after challenge. This indicates that the dogs were persistently infected.

TABLE 1

Serologic Analysis of Dogs for Coinfecting Microorganisms Associated with Ixodes Ticks.

| | Pre-Challenge | | | | | | | Post-Challenge | | | | | | |
|---|---|---|---|---|---|---|---|---|---|---|---|---|---|---|
| Dog i.d. | B. burgdorferi | Ba. canis | Ba. microti | Ba. gibsonii | RMSF | E. canis | E. equi | B. burgdorferi | Ba. canis | Ba. microti | Ba. gibsoni | RMSF | E. canis | E. equi |
| ETP | neg | neg | neg | neg | neg | neg | neg | pos | neg | neg | neg | neg | neg | neg |
| EIP | neg | neg | neg | neg | neg | W +[1] | neg | pos | neg | neg | neg | neg | neg | pos |
| DXP | neg | neg | neg | neg | neg | neg | neg | pos | W + | neg | neg | neg | neg | pos |
| EEP | neg | neg | neg | neg | neg | neg | neg | pos | neg | neg | neg | neg | neg | pos |
| HBP | neg | neg | neg | neg | neg | neg | neg | pos | neg | neg | neg | neg | neg | neg |
| EJO | neg | neg | neg | neg | neg | neg | neg | pos | neg | neg | neg | neg | neg | neg |
| EQO | neg | neg | neg | neg | neg | neg | neg | pos | neg | neg | neg | neg | neg | pos |
| EKO | neg | neg | neg | neg | neg | neg | neg | pos | neg | neg | neg | neg | neg | pos |
| GQO | neg | neg | neg | neg | neg | neg | neg | pos | neg | neg | neg | neg | neg | pos |
| DVO | neg | neg | neg | neg | neg | neg | neg | pos | neg | neg | neg | neg | neg | pos |
| DUO | neg | neg | neg | neg | neg | neg | neg | pos | neg | neg | neg | neg | neg | neg |

[1]W + = "weak positive".

TABLE 2

Hematologic Parameters of Granulocytic Ehrlichia Infected Dogs Before and After Challenge

| | uninf | | tTest inf | infected | |
|---|---|---|---|---|---|
| | AVE | STDV | vs uninf | AVE | STDV |
| PRE CHALLENGE | | | | | |
| WBC × 1000 | 11.34 | 2.68 | 0.643 | 11.88 | 2.45 |
| NEUTROPHILS | 61.0 | 8.2 | 0.953 | 61.2 | 6.8 |
| BANDS | 0 | 0 | inapprop | 0 | 0 |
| EOSINOPHILS | 2.8 | 2.3 | 0.530 | 2.2 | 1.8 |
| LYMPHOCYTES | 27.5 | 6.5 | 0.712 | 28.5 | 5.6 |
| MONOCYTES | 8.70 | 1.34 | 0.623 | 8.20 | 2.86 |
| RBC × 1,000,000 | 6.49 | 0.34 | 0.241 | 6.77 | 0.65 |
| HEMOGLOBIN | 15.35 | 0.93 | 0.249 | 15.84 | 0.91 |
| HCT | 46.73 | 2.58 | 0.438 | 47.83 | 3.54 |
| PLATELET × 1000 | 371 | 53 | 0.718 | 380 | 54 |
| POST CHALLENGE | | | | | |
| WBC × 1000 | 10.11 | 1.18 | 0.849 | 10.27 | 2.35 |
| NEUTROPHILS | 63.4 | 7.9 | 0.013 | 53.8 | 7.8 |
| BANDS | 0 | 0 | inapprop | 0 | 0 |
| EOSINOPHILS | 1.5 | 1.1 | 0.493 | 1.9 | 1.4 |
| LYMPHOCYTES | 29.1 | 6.6 | 0.013 | 38.2 | 8.2 |
| MONOCYTES | 5.00 | 1.89 | 0.191 | 6.10 | 1.73 |
| RBC × 1,000,000 | 6.43 | 0.47 | 0.988 | 6.43 | 0.38 |
| HEMOGLOBIN | 15.43 | 0.89 | 0.981 | 15.42 | 0.92 |
| HCT | 46.99 | 4.18 | 0.662 | 46.3 | 2.12 |
| PLATELET × 1000 | 336 | 55 | 0.350 | 309 | 69 |

EXAMPLE 2

Culture Conditions for Isolation of Granulocytic Ehrlichia

The human promyelocytic leukemia cell line HL-60 (ATCC CCL 240) and the murine monocyte-macrophage line P388D1 (ATCC TIB 63) were used in attempts to isolate the Ehrlichia from blood of dogs challenged with field collected *Ixodes scapularis* ticks.

Cell culture conditions and media were: RPMI 1640 containing 20% heat-inactivated fetal bovine serum, 2 mM 1-glutamine, 1 mM sodium pyruvate, 0.1 mM MEM nonessential amino acids or similar suitable media as required to maintain the host cell line. There were no antibiotics used. Cells were maintained in a 37° C., 5% $CO_2$ incubator (Collins et al., *Nature* 270:347–349 (1977)).

Mammalian cells were cocultured with blood cells from dogs by either of two methods. By method 1, 100 μl or 200 μl of whole blood were added to cultures of either HL60 or P388D1 cells, respectively, By method 2, 100 μl of isolated granulocyte/monocytes from dog blood were added to a tissue culture filter insert suspended over HL60 cells. The filter prevented direct contact of canine cells with the HL60 but would have allowed bacteria or virus to pass through. An Ehrlichia isolate was not obtained from the monocytecrophage line P388D1 but was obtained in several attempts with the promyelocytic leukemia cell line HL60. As shown in Table 3, both methods were used successfully to obtain Ehrlichia isolates. Degenerative cell morphology first became noticeable many passages after coculture. As indicated in Table 3, it was not obvious until at least day 26 that the cells were infected. In all but two cases (VOG and XUG) it was necessary to pass the infected cells over fresh uninfected HL60 cells in order to maintain the culture. Granulocytic Ehrlichia cell lines that produced significant cytopathic effect on the mammalian host cell line had to be split onto fresh cells two to three times per week. A split ration of 1:2 or 1:3 of the cytopathic cell lines onto fresh HL60 is adequate. Nonlytic cell lines (VOG and XUG) grow slightly slower than uninfected HL60 cells but are indistinguishable from HL60 by light microscopy.

To confirm that the cultures were degenerating because of a bacterial contaminant and not a virus, the following experiment was performed. Five of the infected cell lines were grown and in each case either cells (as usual), low speed spin supernatants (mammalian cell free), or 0.2 μm filtered low speed spun supernatants were passaged over healthy HL60 cells. The results are shown in Table 4.

In all five cases, infection was transmitted to uninfected cells by either cell to cell contact or mammalian cell free supernatants but not by filtered mammalian cell free supernatants. Thus, the infectious agent was a bacteria that was larger than 0.2 μm and not a virus.

Figure 2:
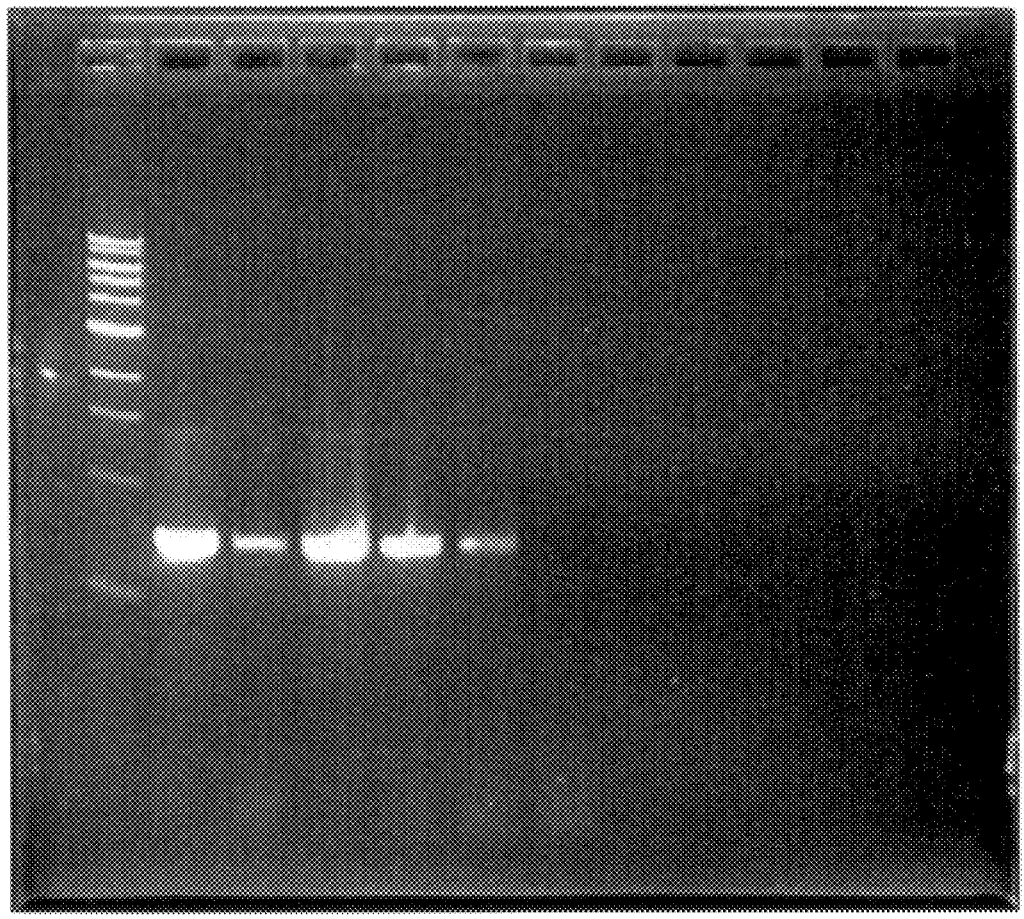
FIG. 2. PCR analysis of granulocytic Ehrlichia infected (XTG, VXG3, USG, XGG, and VBH) and uninfected (HL60) cell lines. PCR of HGE infected HL-60 cells using Ehrlichia specific 16S rRNA probes (Anderson et al., *J. Clin. Micro.* 29:2838–42). Lane 1, molecular weight markers; lane 2, USG3 cells (passage 40); lane 3, XGG3 cells (passage 37); lane 4, VXG3 cells (passage 39); lane 5, VBH3 (passage 39); lane 6, XTG3 cells (passage 36); and lane 7, uninfected HL-60 cells.

PCR was used to confirm the presence of Ehrlichia in the infected (XTG, VXG3, XGG, and VBH) and the absence of Ehrlichia in the uninfected (HL60) cell lines (FIG. 2). Primers were used that are known to be specific for the 16rRNA gene of ≧90 percent of Ehrlichia species (Anderson et al., *J. Clin. Microbiol.* 29:2838–2842 (1991)).

Figure 3A:
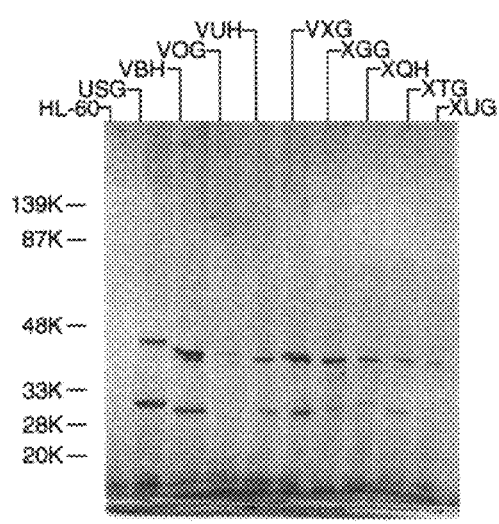
FIG. 3. Western blot using sera from granulocytic Ehrlichia infected (A) or uninfected (B) dogs. The antigens used in each lane are the lysed cells of HL-60, USG, VBH, VOG, VUH, VXG, XGG, XQH, XTG, and XUG.
Figure 3B:
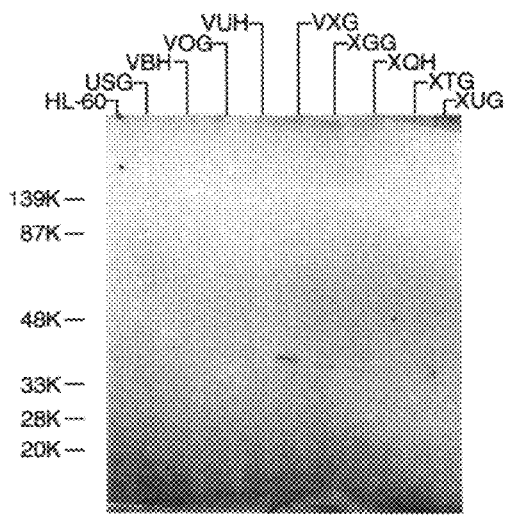

For subsequent analysis by SDS-PAGE and Western blot, approximately $1 \times 10^6$ infected mammalian cells of the indicated cell lines were harvested, washed, and lysed. The results shown in FIG. 3 demonstrate that at least three antigens were detectable for infected but not uninfected cell lysates. Detection was accomplished using canine sera from an granulocytic Ehrlichia infected dog (UKG) from the experimental challenge which was not among those used to obtain cell lines.

SDS-PAGE and Western blot analysis can also be applied to granulocytic Ehrlichia antigens present in mammalian cell free supernatants of the cell line VXG3 (Table 5). Antigens collected by high speed centrifugation from approximately 100 ml of VXG3 mammalian cell free supernatants were applied to a ten percent SDS-PAGE gel and then Western blotted with dog serum. Seven antigens, with apparent molecular weights of 21 kD, 23 kDa, 47 kDa, 85 kDa, 130 kDa, and 145 kDa were observed. Although weak reactivity was seen with a few nonimmune sera, these antigens alone or in combination had good positive and negative predictive values and can serve as diagnostic proteins for granulocytic infection. Any of these proteins, synthetic peptides, fragments or recombinant antigens equivalent to them, can be used as a vaccine for the prevention of granulocytic ehrlichiosis.

A human granulocytic cell line has been infected with an Ehrlichia found in the blood of dogs challenged with *I. scapularis*. Antigens in this cultured Ehrlichia cross react serologically with *E. equi*. There are no reports of culture conditions suitable for *E. equi*. Antigens from infected cell extracts or culture supernatants have been used to detect antibodies from dogs infected with this granulocytic Ehrlichia.

TABLE 3

Characteristics of Cell Lines Used in the Isolation of Granulocytic Ehrlichia

| CBC Cell Line Designation | Donor Dog I.D. | Isolation Method | Passage # (day) After Coculture when Cells Began to Degenerate | Cultivation Characteristics | ATCC No. |
|---|---|---|---|---|---|
| HL-60 | not relevant | not relevant | no degeneration | normal* | CCL 240 |
| USG | USG3 | method 1 | 11 (35) | special | |
| VBH | VBH3 | method 1 | 8 (26) | special | |
| VOG | VOG3 | method 1 | 16 (53) | normal | |
| VXG | VXG3 | method 1 | 12 (39) | special | CRL-11865 |
| XGG | XGG3 | method 1 | 8 (26) | special | |
| XTG | XTG3 | method 1 | 9 (28) | special | |
| XQH | XQH | method 2 | 11 (39) | special | CRL-11864 |
| VUH | VUH | method 2 | 13 (46) | special | |
| XUG | XUG | method 2 | 15 (56) | normal | |

*normal = Does not require special growth conditions. Culture can be maintained without splitting over fresh cells.
special = Requires culture to be split over fresh HL-60 for viability of host cells.

TABLE 4

Characteristics of the Transmission of Granulocytic Ehrlichia in Cell Culture

| | Status of HL60 Cells after Coculture (day observed) | | |
|---|---|---|---|
| Cell Line | Direct Passage of Infected Cells onto HL60 | Supernatant of Infected Cells Added to HL60 | Filtered Supernatant of Infected Cells Added to HL60 |
| USG | sick (2) | sick (10) | healthy (25) |
| XGG | sick (2) | sick (18) | healthy (25) |
| VXG | sick (2) | sick (10) | healthy (25) |
| VBH | sick (2) | sick (10) | healthy (25) |
| XTG | sick (2) | sick (18) | healthy (25) |

TABLE 5

Western blot reactivity patterns of sera from granulocytic Ehrlichia infected (post-challenge) and uninfected (pre-challenge) dogs with granulocytic Ehrlichia antigens from the cell line VXG3.

| Dog i.d. | Serum collection | Western blot reactivity with VXG3 antigens | | | | | | |
|---|---|---|---|---|---|---|---|---|
| | | 21 | 23 | 40 | 47 | 85 | 130 | 145 |
| UHG | pre-challenge | | | | | | | |
| UHG | post-challenge | | W | S | | S | S | |
| UQH | pre-challenge | | | | | | | |
| UQH | post-challenge | | | S | | M | M | |
| USG | pre-challenge | | | | | | | |
| USG | post-challenge | | | S | S | S | S | |
| VBH | pre-challenge | | W | | | | | |
| VBH | post-challenge | | W | | S | S | S | S |
| VKG | pre-challenge | | | | W | | | |
| VKG | post-challenge | W | | W | | | W | |
| VOG | pre-challenge | | | | | | | |
| VOG | post-challenge | S | W | | S | S | S | W |
| VXG | pre-challenge | | | | W | | | |
| VXG | post-challenge | | | W | S | S | S | S |
| WAH | pre-challenge | | | | | | | |
| WAH | post-challenge | W | | S | S | S | S | M |
| XGG | pre-challenge | | | | | M | | |
| XGG | post-challenge | | | W | S | W | S | |
| XTG | pre-challenge | | | | | | | |
| XTG | post-challenge | | | W | S | W | S | |
| pos. predictive value | | 100% | 67% | 100% | 91% | 78% | 100% | 100% |
| neg. predictive value | | 59% | 53% | 67% | 100% | 73% | 91% | 83% |
| Protein Intensity | | W | W | M | S | M | M | W |

W = weak; M = moderate; S = strong

EXAMPLE 3

Alternate Host Cell Lines for Maintenance of Granulocytic Ehrlichia

The range of host cell infectability was analyzed by assembling a panel of human, monkey, canine, and murine cell lines derived from various tissues and representing various stages of differentiation.

Materials and Methods

A number of uninfected cell lines were obtained from ATCC and maintained in tissue culture as described in Example 2. Each cell line was tested for the ability to act as a host for granulocytic Ehrlichia by coculture with $5\times10^5$ cells of USG and separately by coculture with $5\times10^5$ cells of VXG cells. Under these conditions, USG and VXG cells would be completely lysed within a few days. All subsequent culture splits were done in fresh media. Cells were maintained in coculture for 4 weeks and morphology observed. Uninfected cell line were maintained in culture in a parallel fashion as a control. Samples of each test cell line were analyzed by PCR using the method described in Example 2.

Results

The results of the granulocytic transmission experiment are shown in Table 6. Six of the eleven cell lines could be infected. Infection was demonstrated in five of the six cell lines (HL-60, KG1, U937, THP-1, and HEL299) by changes in cell morphology as well as by PCR analysis. An additional cell line, AML-193, showed strong cytopathology within the four week observation period and was very likely infected but PCR was not performed. Four of the cell lines (DH82, Vero, P388D1, and IC-21) gave no indication of infection either by changes in cell morphology or by PCR. One cell line, JM1, developed unusual cellular morphology shortly after coculture but then reverted to its normal macrophage-like form and the PCR result was negative.

Discussion

The ability of granulocytic Ehrlichia to infect the human promyelocytic leukemia cell line HL-60 is consistent with the known cellular tropism of the bacteria in infected human patients. The ability of granulocytic Ehrlichia, that had been originally isolated in the promyelocytic leukemia cell line HL-60 to transmit infection to other cell lines with different phenotypes was analyzed. The ability of HL-60 derived granulocytic Ehrlichia to infect the human acute myelogenous leukemia cell line, KG-1, is consistent with the tendency for the organism to infect granulocytic cell or cells that can further differentiate into granulocytic cells.

HL-60 derived granulocytic Ehrlichia are also able to infect human cell lines that are more differentiated toward a monocytic phenotype such as, U937, THP-1, or AML-193. U937 has been previously used as a host cell line for *E. risticii*.

HL-60 derived granulocytic Ehrlichia were also able to infect the human embryonic lung cell line, HEL299. The infectability of this cell line is fortuitous since HEL299 are an attached fibroblast like cell line that has the potential to be used in plaque assays for infectivity assays.

The inability to infect a canine monocytic cell line, DH-82, with HL-60 derived granulocytic Ehrlichia is interesting in that this cell line can act as a host for several monocytic Ehrlichia including *E. canis, E. chaffeensis*, and *E. muris*. Similarly, the inability to infect the monocyte-lymphoblast-like cell line, P388D1, with HL-60 derived granulocytic Ehrlichia is interesting since this cell line has been used as a host for *E. risticii*, a monocytic Ehrlichia. A similar conclusion could be reached with regard to the murine macrophage cell line, IC-21.

The inability to infect the human pre-B cell line, JM-1, with HL-60 derived granulocytic Ehrlichia is not surprising since this cellular phenotype has not been identified as a target for infection by any known Ehrlichia. The African green monkey kidney cell line, Vero, would also have been an unlikely host for infection with HL-60 derived granulocytic Ehrlichia.

made without departing from the true scope of the invention and appended claims.

What is claimed is:

1. A method of continually growing human granulocytic Ehrlichia, *E. equi*, or *E. phagocytophila* comprising a) infecting a cell line, wherein the phenotype of the cell line is selected from the group consisting of a promelocytic leukemia cell line, an acute myelogenous leukemia cell line, a histiocytic lymphoma cell line, an acute monocytic leukemia cell line, and an embryonic lung cell line, with human granulocytic Ehrlichia, *E. equi*, or *E. phagocylophila* by co-culturing the cell line with blood cells infected with human granulocytic Ehrlichia, *E. equi*, or *E. phagocytophila* within a suitable culture medium;

b) culturing the infected cell line with fresh uninfected cultured cells;

c) splitting the infected cell line in a split ratio of about 1:2 or 1:3 of infected cells to additional said fresh uninfected cultured cells in order to maintain the culture; and d) identifying a cytopathic effect on the infected cell line, wherein the means for identifying the cytopathic effect comprise i) using an immunofluorescence assay, Western blot analysis, EIA or RIA to detect the presence of human granulocytic Ehrlichia, *E. equi* or *E. phagocytophila* using detector antibodies specific for said human granulocytic Ehrlichia, *E. equi* or *E. phagocytophila*;

TABLE 6

Transmission of granulocytic Ehrlichia from infected HL-60 cells to other cell lines.

| Cell line, ATCC designation | Cell type and normal cellular morphology | Cellular morphology following coculture with granulocytic Ehrlichia derived from‡ | | PCR results @ |
|---|---|---|---|---|
| | | USG Cells | VXG cells | |
| HL-60, ATCC CCL-240 | Human promyelocytic leukemia, lymphoblast-like | Strong cytopathology | Strong cytopathology | Positive |
| KG-1, ATCC CCL-246 | Human acute myelogenous leukemia, myeloblast-like | Abnormal growth | Abnormal growth | Positive |
| U937, ATCC CRL-1593.2 | Human histiocytic lymphoma, monocyte-like | Abnormal growth | Abnormal growth | Positive |
| THP-1, ATCC TIB-202 | Human monocyte, macrophage-like | Strong cytopathology | Strong cytopathology | Positive |
| AML-193, ATCC CRL-9589 | Human acute monocytic leukemia, lymphoblast-like | Strong cytopathology | Strong cytopathology | Not done |
| HEL299, ATCC CCL-137 | Human embryonic lang cells, attached fibroblast-like | Strong cytopathology | Strong cytopathology | Positive |
| DH82, ATCC CRL-10389 | Canine, monocyte-macrophage-like | Unaffected | Unaffected | Negative |
| JM1, ATCC CRL-10423 | Human Pre-B cell, macrophage-like | Abnormal but later became normal | Not done | Negative |
| Vero, ATCC CCL-81 | African green monkey kidney cell, fibroblast-like | Unaffected | Unaffected | Negative |
| P388D1, ATCC TIB-63 | Murine lymphoid neoplasm, lymphoblast-like | Unaffected | Unaffected | Negative |
| IC-21, ATCC TIB-186 | Murine, macrophage-like | Unaffected | Unaffected | Negative |

‡All cell lines were cocultured with USG and VXG except JM1 which was cocultured with only USG.
@ PGR results are based upon data obtained from cell lines cocultured with USG using the PCR primer pair GE9 and GE10. PCR was not performed on cell lines following coculture with VXG.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be ii) using PCR or RFLP to confirm the presence or absence of human granulocytic Ehrlichia, *E. equi* or *E. phagocytophila* in the cell lines with a primer specific or a 16S rDNA gene specific for said human granulocytic Ehrlichia, *E. equi* or *E. phagocytophila*; or iii) observing degenerative cell morphology by light microscopy.

2. The method according to claim 1 wherein the phenotype of the cell line is selected from the group consisting of a promyelocytic leukemia cell line, an acute myelogenous leukemia cell line, a histiocytic lymphoma cell line, an acute monocytic leukemia cell line, and an embryonic lung cell line.

3. The method according to claim 2 wherein the culture medium comprises RPMI 1640 containing 10%–20% heat-inactivated fetal bovine serum, 2 mM l-glutamine, 1 mM sodium pyruvate, and 0.1 mM MEM non-essential amino acids.

4. The method of continually growing human granulocytic Ehrlichia, *E. equi* or *E. phagocytophila* according to claim 1 wherein step a) further comprises adding whole blood from canines who had been challenged with *Ixodes scapularis* ticks to cultures of the cell line.

5. The method of continually growing human granulocytic Ehrlichia, *E. equi*, or *E. phagocytophila* according to claim 1 wherein step a) further comprises adding isolated granulocytes/monocytes from blood of canines who had been challenged with *Ixodes scapularis* ticks to a tissue culture filter insert suspended over cultures of the cell line.

6. The method according to claim 2 wherein the cell line is a human cell line.

7. The method according to claim 6 wherein the human promyelocytic leukemia cell line is HL-60 (ATCC CCL 240) or mutants or variants thereof.

8. The method according to claim 7 wherein the infected HL-60 cell line has the identifying characteristics of cell line XQH (ATCC CRL-11864) or mutants or variants thereof.

9. The method according to claim 7 wherein the infected HL-60 cell line has the identifying characteristics of cell line VXG3 (ATCC CRL-11865) or mutants or variants thereof.

10. The method according to claim 2 wherein the human acute myelogenous leukemia cell line is KG-1 (ATCC CRL-246) or mutants or variants thereof.

11. The method according to claim 2 wherein the human histiocytic lymphoma cell line is U937 (ATCC CRL-1593.2) or mutants or variants thereof.

12. The method according to claim 2 wherein the human acute monocytic leukemia cell line is AML-193 (ATCC CRL-9589) or mutants or variants thereof.

13. The method according to claim 2 wherein the human embryonic lung cell line is HEL299 (ATCC CCL-137) or mutants or variants thereof.

14. A method of purifying human granulocytic Ehrlichia, *E. equi*, or *E. phagocytophila* comprising
   a) continually growing human granulocytic Ehrlichia, *E. equi*, or *E. phagocytophila* according to the method of claim 1; and
   purifying the human granulocytic Ehrlichia, *E. equi* or *E. phagocytophila* from the infected cell line.

15. The method according to claim 14 wherein step b) further comprises harvesting, washing, and lysing infected cells of the cell line and preparing cell free supernatants by high speed centrifugation, and analyzing the human granulocytic Ehrlichia, *E. equi*, or *E. phagocytophila* by SDS-PAGE and Western blot analysis.

16. The method according to claim 14 wherein the phenotype of the cell line is selected from the group consisting of a promyelocytic leukemia cell line, an acute myelogenous leukemia cell line, a histiocytic lymphoma cell line, an acute monocytic leukemia cell line, and an embryonic lung cell line.

17. The method according to claim 16 wherein the cell line is a human cell line.

18. The method according to claim 17 wherein the human promyelocytic leukemia cell line is HL-60 (ATCC CCL 240) or mutants or variants thereof.

19. The method according to claim 18 wherein the infected HL-60 cell line has the identifying characteristics of cell line XQH (ATCC CRL-11864) or mutants or variants thereof.

20. The method according to claim 18 wherein the infected HL-60 cell line has the identifying characteristics of cell line VXG3 (ATCC CRL-11865) or mutants or variants thereof.

21. The method according to claim 17 where the human acute myelogenous cell line is KG-1 (ATCC CCL-246) or mutants or variants thereof.

22. The method according to claim 17 wherein the human histiocytic lymphoma cell line is U937 (ATCC CRL-1593.2) or mutants or variants thereof.

23. The method according to claim 17 wherein the human acute monocytic leukemia cell line is AML-193 (ATCC CRL-9589) or mutants or variants thereof.

24. The method according to claim 17 wherein the human embryonic lung cell line is HEL299 (ATCC CCL-137) or mutants or variants thereof.

25. A cell line cultured according to the method of claim 1 wherein the phenotype of the cell line is selected from the group consisting of a promyelocytic leukemia cell line, an acute myelogenous leukemia cell line, a histiocytic lymphoma cell line, an acute monocytic leukemia cell line, and an embryonic lung cell line.

26. The cell line according to claim 25 wherein the cell line is a human cell line.

27. The cell line according to claim 26 wherein the human promyelocytic leukemia cell line is HL-60 (ATCC CCL 240) or mutants or variants thereof.

28. The cell line according to claim 27 wherein the infected HL-60 cell line has the identifying characteristics of cell line XQH (ATCC CRL-11864) or mutants or variants thereof.

29. The cell line according to claim 27 wherein the infected HL-60 cell line has the identifying characteristics of cell line VXG3 (ATCC CRL-11865) or mutants or variants thereof.

30. The cell line according to claim 26 wherein the human acute myelogenous leukemia cell line is KG-1 (ATCC CCL-246) or mutants or variants thereof.

31. The cell line according to claim 26 wherein the human histiocytic lymphoma cell line is U937 (ATCC CRL-1593.2) or mutants or variants thereof.

32. The cell line according to claim 26 wherein the human acute monocytic leukemia cell line is AML-193 (ATCC CRL-9589) or mutants or variants thereof.

33. The cell line according to claim 26 wherein the human embryonic lung cell line is HEL299 (ATCC CCL-137) or mutants or variants thereof.

34. The method of continually growing human granulocytic Ehrlichia, *E. equi* or *E. phagocytophila* according to claim 1, wherein the degenerative cell morphology comprises cell lysis, cell clumping, or the formation of plaques.

* * * * *